United States Patent
Abekawa et al.

(10) Patent No.: US 7,081,426 B2
(45) Date of Patent: Jul. 25, 2006

(54) METHOD FOR IMPROVING CRYSTALLINE TITANOSILICATE CATALYST HAVING MWW STRUCTURE

(75) Inventors: Hiroaki Abekawa, Toyonaka (JP); Masaru Ishino, Chiba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/506,645

(22) PCT Filed: Feb. 28, 2003

(86) PCT No.: PCT/JP03/02289

§ 371 (c)(1),
(2), (4) Date: Sep. 3, 2004

(87) PCT Pub. No.: WO03/074179

PCT Pub. Date: Sep. 12, 2003

(65) Prior Publication Data
US 2005/0227852 A1 Oct. 13, 2005

(30) Foreign Application Priority Data
Mar. 4, 2002 (JP) ............................. 2002-056908

(51) Int. Cl.
*B01J 29/06* (2006.01)
(52) U.S. Cl. ............................. 502/62; 502/64; 502/85
(58) Field of Classification Search .................... None
See application file for complete search history.

(56) References Cited

U.S. PATENT DOCUMENTS

| | | | |
|---|---|---|---|
| 4,824,976 A | 4/1989 | Clerici et al. | |
| 4,937,216 A | 6/1990 | Clerici et al. | |
| 4,954,325 A | 9/1990 | Rubin et al. | |
| 5,840,650 A | 11/1998 | Tamura et al. | |
| 6,106,797 A | 8/2000 | Müller et al. | |
| 6,114,551 A | 9/2000 | Levin et al. | |
| 6,734,133 B1 * | 5/2004 | Weisbeck et al. | 502/119 |
| 6,740,764 B1 | 5/2004 | Chen et al. | |
| 6,759,540 B1 * | 7/2004 | Oguchi et al. | 549/529 |
| 2003/0049305 A1 * | 3/2003 | Lipinski et al. | 424/439 |

FOREIGN PATENT DOCUMENTS

| | | |
|---|---|---|
| EP | 1048639 A1 | 11/2000 |
| JP | 62-185081 A | 8/1987 |
| JP | 8-269031 A | 10/1996 |
| WO | WO 99/26936 A2 | 6/1999 |
| WO | WO 00/64582 A1 | 11/2000 |
| WO | WO 01/34298 A1 | 5/2001 |
| WO | WO 03/074421 A1 | 9/2003 |

OTHER PUBLICATIONS

Wu, P., et al., "Hydrothermal synthesis of a novel titanosilicate with MWW topology", Chem. Lett., vol. 7, pp. 774-775 (2000).
Wu, P., et al., "Extremely high *trans* selectively of Ti-MWW in epoxidation of alkenes with hydrogen peroxide", *Chem. Comm.*, pp. 897-898 (2001).
Wu, P., et al., "A novel titanosilicate with MWW structure, I. Hydrothermal Synthesis, Elimination of Extraframework Titanium, and Characterizations", *J. Phys. Chem. B.*, vol. 105, pp. 2897-2905 (2001).
Shokubai, "Postsynthesis Ti-MWW", Catalysts and Catalysts, vol. 44, No. 6, pp. 468-470 (2002).
Clerici, M.G., et al., "Synthesis of propylene oxide from propylene and hydrogen peroxide catalyzed by titanium silicalite", *J. Catalysis*, vol. 129, pp. 159-167 (1991).
Thangaraj, A., "Catalytic properties of crystalline titanium silicates", *J. Catalysis*, 130, pp. 1-8 (1991).
Proceedings of the 88th Catalysis Society of Japan Meeting A, p. 154 (2001).
Proceedings of the 89th Catalysis Society of Japan Meeting A, p. 65 (2002).
Report of R&D projects for "Next-generation Chemical Process Technology /Non-halogen Chemical Process Technology" FY2000 Annual Report, pp. 261-168, (2001).
Report of R&D projects for "Next-generation Chemical Process Technology /Non-halogen Chemical Process Technology" FY2001 Annual Report, pp. 168-209, (2002).

* cited by examiner

*Primary Examiner*—Christina Johnson
(74) *Attorney, Agent, or Firm*—Akin Gump Strauss Hauer & Feld, LLP

(57) ABSTRACT

A method for improving a crystalline titanosilicate catalyst having an MWW structure, characterized in that it comprises treating the crystalline titanosilicate catalyst having a MWW structure with a silylating agent.

8 Claims, No Drawings

METHOD FOR IMPROVING CRYSTALLINE TITANOSILICATE CATALYST HAVING MWW STRUCTURE

CROSS-REFERENCE TO RELATED APPLICATION

This application is a Section 371 of International Application No. PCT/JP03/002289, filed Feb. 28, 2003, the disclosure of which is incorporated herein by reference.

FIELD OF THE INVENTION

The present invention relates to a method for improving a crystalline titanosilicate catalyst having an MWW structure. More specifically, the present invention relates to a method for improving a catalyst, which method is capable of efficiently activating a crystalline titanosilicate catalyst having an MWW structure.

BACKGROUND ART

Various crystalline titanosilicate catalysts are known and some of them are known as being effective catalysts for the production of epoxy compounds by epoxidation of olefins, the productions of phenol compounds or polyhydroxyphenyl compounds by hydroxylation reactions, of benzene or phenol compounds, respectively, or the like.

In addition, the present invention relates to a crystalline titanosilicate catalyst having an MWW structure. The MWW structure is a framework type code name specified by International Zeolite Association (IZA). A crystalline metallosilicate (zeolite) having an MWW structure is known as the name of MCM-22. Therefore a crystalline titanosilicate catalyst having an MWW structure, which contains titanium (hereinafter referred to as Ti) within the framework, is known as the name of Ti-MWW, or Ti-MCM-22, or the like.

Additionally, this crystalline titanosilicate having an MWW structure is also known to be a useful material as a catalyst.

Generally, enhancing the activity of a catalyst can lead to reduction of the amount of the catalyst and thus reduction of the catalyst cost, and also to lower the cost of reaction vessel by reducing its size, and therefore further enhancement of the catalyst activity of the Ti-MWW catalyst is also desired.

As a method of highly activating the Ti-MWW catalyst, a method of increasing the Ti content is known (e.g., Chemical Communication 897, (2001)), but it is known that a high Ti content with the Ti to Si (silicon) ratio being 1/40 or more deteriorates the crystallinity of the Ti-MWW catalyst (e.g., Journal of Physical Chemistry B, 105, 2897, (2001)). In general, with a crystalline titanosilicate catalyst, poorer crystallinity is accompanied by lesser catalyst performance in some cases. As such, a novel method of highly enhancing the activity of a catalyst except for increase of Ti content is needed.

DISCLOSURE OF THE INVENTION

The object of the present invention is to provide a method for improving a catalyst, which method is capable of efficiently enhancing the catalytic activity of a crystalline titanosilicate catalyst having an MWW structure.

In other words, the present invention relates to a method of improving a crystalline titanosilicate catalyst having an MWW structure, characterized in that it comprises treating the crystalline titanosilicate catalyst having an MWW structure with a silylating agent.

BEST MODE FOR CARRYING OUT THE INVENTION

Examples of the method for producing a crystalline titanosilicate catalyst having an MWW structure include the following methods.

That is, there are known a method that involves contacting with $TiCl_4$ a crystalline aluminosilicate catalyst having an MWW structure(hereinafter referred to as Al-MWW), and substituting aluminum (hereinafter referred to as Al) with Ti to incorporate Ti as described in U.S. Pat. No. 6,114,551; a method of hydrothermal synthesis using a titanium alkoxide as described in Chemistry Letters 774, (2000); a method that involves once crystallizing, delaminating the layers of the crystal, thereby collapsing the crystal, and then incorporating Ti to crystallize again as described in Shokubai (Catalysts & Catalysis) 44, 6, 468, (2002); or a method of synthesis by means of the dry gel conversion process using a titanium alkoxide as described in the proceedings of the 88th Catalysis Society of Japan (CatSJ) Meeting A", 154, (2001).

It is preferable on account of a higher activity that a Ti-MWW catalyst used in silylation is a Ti-MWW catalyst containing Ti having been incorporated during crystallization.

The methods for preparing a Ti-MWW catalyst containing Ti having been incorporated during crystallization include a method that involves hydrothermal synthesis through the use of a titanium alkoxide; a method that involves once crystallizing, delaminating the layers of the resulting crystals, thereby collapsing the crystal, then incorporating Ti, and crystallizing again; and the dry gel conversion method with a titanium alkoxide; and the like.

In addition, when a Ti-MWW catalyst is prepared using Al as for the method in which $TiCl_4$ is made to contact with an Al-MWW catalyst described in U.S. Pat. No. 6,114,551, since the residual Al acts as acidity that induces a side reaction in some cases, a method without using Al is preferable.

In the present invention, a crystalline titanosilicate having an MWW structure, that is, a Ti-MWW catalyst is treated with a silylating agent.

The silylating agents include, for example, silylamine compounds such as 1,1,1,3,3,3-hexamethyldisilazane, (N,N-dimethylamino)trimethylsilane, N-(trimethylsilyl)imidazole or the like, chlorosilane compounds such as trimethylchlorosilane, t-butyldimethylchlorosilane or the like, acetamide compounds such as N,O-bis(trimethylsilyl)acetamide, N-(trimethylsilyl)acetamide, trimethylsilyldiphenyl urea, bis(trimethylsilyl)trifluoroacetamide, and the like. Particularly preferred are 1,1,1,3,3,3-hexamethyldisilazane and trimethylchlorosilane.

Methods of treating the Ti-MWW catalyst with the silylating agent may be any method that allows the catalyst to contact with the silylating agent, and for instance, examples thereof include the following method. That is, the silylation treatment is carried out by mixing the catalyst and the silylating agent. An organic solvent may be used for the treatment, if necessary, and it may be conducted under heating, if necessary. Heating an complete the silylation treatment in a short period of time. The treatment temperature is not particularly limited, but normally from 20° C. to 200° C. Usually, further filtration and washing followed by drying provide the Ti-MWW catalyst treated by silylation. Organic solvents that may be used, if necessary, for the treatment include aromatic hydrocarbon compounds such as toluene, nitrile compounds such as acetonitrile, aliphatic hydrocarbon compounds such as n-heptane, ether compounds such as tetrahydrofuran, amide compounds such as dimethylformamide, cyclic amine compounds such as pyridine, amine compounds such as triethylamine, and the like. Also, when a silylating agent containing chlorine such as trimethylchlorosilane is used, a basic organic solvent such as pyridine or triethylamine is preferably used.

The catalyst of which activity is enhanced by the present invention can suitably be used for epoxidation reactions of olefins using hydrogen peroxide, or hydroxylation reactions of benzenes or phenol compounds using hydrogen peroxide. Epoxidation reactions of olefins using hydrogen peroxide can particularly suitably be used for the epoxidation reaction of propylene.

Methods of supplying hydrogen peroxide include a method of supplying a hydrogen peroxide solution produced in advance, a method of supplying in-situ synthesized hydrogen peroxide from hydrogen and oxygen, and the like. Methods of synthesizing hydrogen peroxide in the reaction system, in-situ, include a method of synthesizing hydrogen peroxide by using transition metal catalyst such as Pd(palladium), or Au(gold) for synthesizing hydrogen peroxide from hydrogen and oxygen in-situ, mixed with or supported on the Ti-MWW catalyst.

The aforementioned reaction can be carried out in the presence of an organic solvent, if necessary. The organic solvent can also be used by mixing with an inorganic solvent such as water, or with an inorganic compound in a supercritical state such as carbon dioxide in a supercritical state. The organic solvents that may be used include a hydrocarbon, a halogenated hydrocarbon, an alcohol, a ketone compound, an ether compound, an ester compound, a nitrile compound, and the like. Preferred organic solvents are nitrile compounds. A preferred nitrile compound is acetonitrile.

In addition, the reaction methods using the activated catalyst of the present invention include a fixed bed flow reaction method and a slurry reaction method.

EXAMPLES

Example 1

Treatment with a silylating agent was carried out using a Ti-MWW catalyst having a Ti content of 1.0% by weight as determined by ICP emission spectrometry, prepared in accordance with the method described in Chemistry Letters 774, (2000).

Silylation was conducted by mixing 3.4 g of 1,1,1,3,3,3-hexamethyldisilazane, 50 g of toluene and 5 g of the Ti-MWW catalyst and refluxing the mixture for 1.5 h. Further, after filtration and washing, dried under reduced pressure at 120° C. to yield the silylated Ti-MWW catalyst.

Then, a reaction was carried out using the resultant silylated Ti-MWW catalyst. That is, a solution of $H_2O_2$: 5% by weight, water: 47.5% by weight and acetonitrile: 47.5% by weight was prepared with an aqueous 60% $H_2O_2$ solution (product of Mitsubishi Gas Chemical Co., Inc.), acetonitrile and purified water. 12 Grams of the solution prepared and 0.010 g of the silylated Ti-MWW catalyst were loaded into a 50 ml stainless steel autoclave. Thereafter, the autoclave was transferred onto an ice water bath, and was loaded with 10 g of liquefied propylene. Furthermore, the pressure was increased to 2 MPa-G with nitrogen. The reaction was deemed started when 5 minutes passed after the autoclave had been placed in hot water bath maintained at 40° C., the inside temperature reaching about 35° C. One hour after the reaction starting, the autoclave was taken out of the warm water bath and sampling was conducted. The analysis was carried out by gas chromatography. As a result, the propylene oxide formation activity per catalyst weight was 0.510 $mol·h^{-1}·g^{-1}$. The propylene oxide selectivity based on propylene was 99.8%.

Example 2

A reaction and analysis were carried out in accordance with the method in Example 1 with the exception that acetone was used instead of acetonitrile.

As a result, the propylene oxide formation activity per catalyst weight was 0.363 $mol·h^{-1}·g^{-1}$. The propylene oxide selectivity based on propylene was 99.2%.

Comparative Example 1

A reaction and an analysis were carried out in accordance with the method in Example 1 with the exception that an unsilylated catalyst of the catalyst used in Example 1 and thus the Ti-MWW catalyst that was not silylated was used.

As a result, the propylene oxide formation activity per catalyst weight was 0.463 $mol·h^{-1}·g^{-1}$. The propylene oxide selectivity based on propylene was 99.9%.

Comparative Example 2

A reaction and analysis were carried out in accordance with the method in Example 2 with the exception that an unsilylated catalyst of the catalyst used in Example 2 and thus the Ti-MWW catalyst that was not silylated was used.

As a result, the propylene oxide formation activity per catalyst weight was 0.230 $mol·h^{-1}·g^{-1}$. The propylene oxide selectivity based on propylene was 98.4%.

INDUSTRIAL APPLICATION

As described above, the present invention can provide a method for improving a catalyst, capable of efficiently activating a crystalline titanosilicate catalyst having a MWW structure.

The invention claimed is:

1. A method for improving a crystalline titanosilicate catalyst having an MWW structure, comprising treating the crystalline titanosilicate catalyst having a MWW structure with a silylating agent to produce a silylated crystalline titanosilicate catalyst having a MWW structure.

2. The method according to claim 1, wherein the crystalline titanosilicate catalyst having an MWW structure is a catalyst containing Ti having been incorporated during crystallization.

3. The method according to claim 1, wherein the catalyst is a catalyst used for epoxidation reaction of an olefin with hydrogen peroxide or a catalyst used for hydroxylation reaction of a benzene or a phenol compound with hydrogen peroxide.

4. The method according to claim 1, wherein the catalyst is a catalyst used for the epoxidation reaction of propylene with hydrogen peroxide.

5. The method according to claim 1, wherein the catalyst is a catalyst used for a reaction utilizing a nitrile compound as a solvent.

6. The method according to claim 2, wherein the catalyst is a catalyst used for epoxidation reaction of an olefin with hydrogen peroxide or a catalyst used for hydroxylation reaction of a benzene or a phenol compound with hydrogen peroxide.

7. The method according to claim 2, wherein the catalyst is a catalyst used for a reaction utilizing a nitrile compound as a solvent.

8. The method according to claim 2, wherein the catalyst is a catalyst used for the epoxidation reaction of propylene with hydrogen peroxide.

* * * * *